United States Patent [19]

Simor

[11] 4,185,385
[45] Jan. 29, 1980

[54] CONTROL SYSTEM FOR DENTAL DRILLS

[75] Inventor: Anton A. Simor, North Vancouver, Canada

[73] Assignee: Den-tal-ez of Canada Ltd., North Vancouver, Canada

[21] Appl. No.: 850,632

[22] Filed: Nov. 11, 1977

[30] Foreign Application Priority Data

Jan. 6, 1977 [GB] United Kingdom ............... 449/77

[51] Int. Cl.² ........................................... A61C 19/02
[52] U.S. Cl. ....................................... 433/28; 433/107
[58] Field of Search .................. 32/22, DIG. 3, 27; 137/842

[56] References Cited

U.S. PATENT DOCUMENTS 4,069,587 1/1978 Peraita ........................................ 32/22

Primary Examiner—Robert Peshock
Attorney, Agent, or Firm—Carver and Company

[57] ABSTRACT

A control assembly for a dental apparatus wherein delivery of operating air, coolant air and coolant water to the dental hand piece is controlled through the operation of normally spring closed pilot valves which are operated to the open position by application of pilot air, delivery of which from the source of pressurized air is controlled by a foot operated valve so as to ensure delivery of coolant air or coolant water when needed when operating air is being delivered to the hand piece.

3 Claims, 5 Drawing Figures

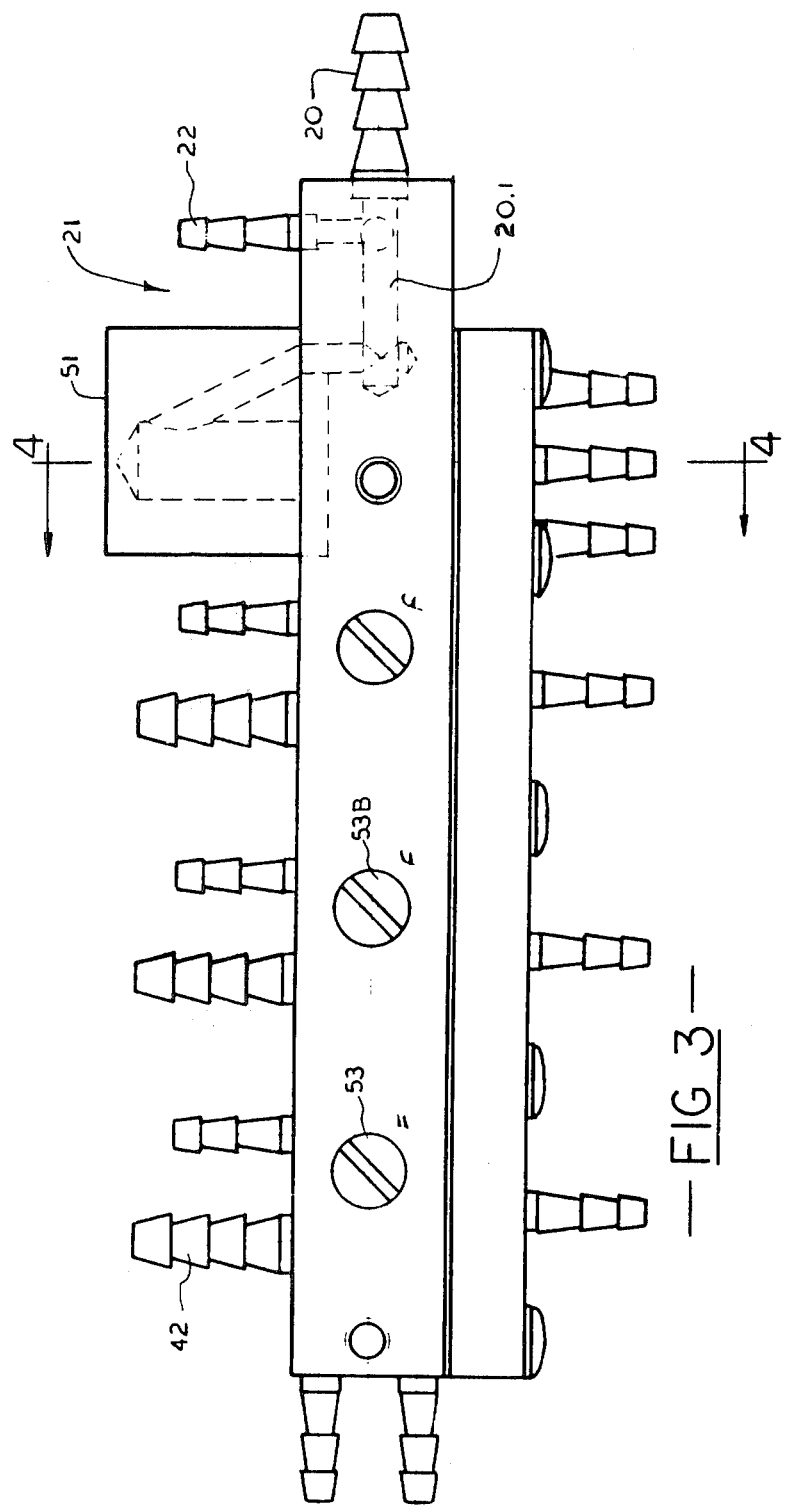

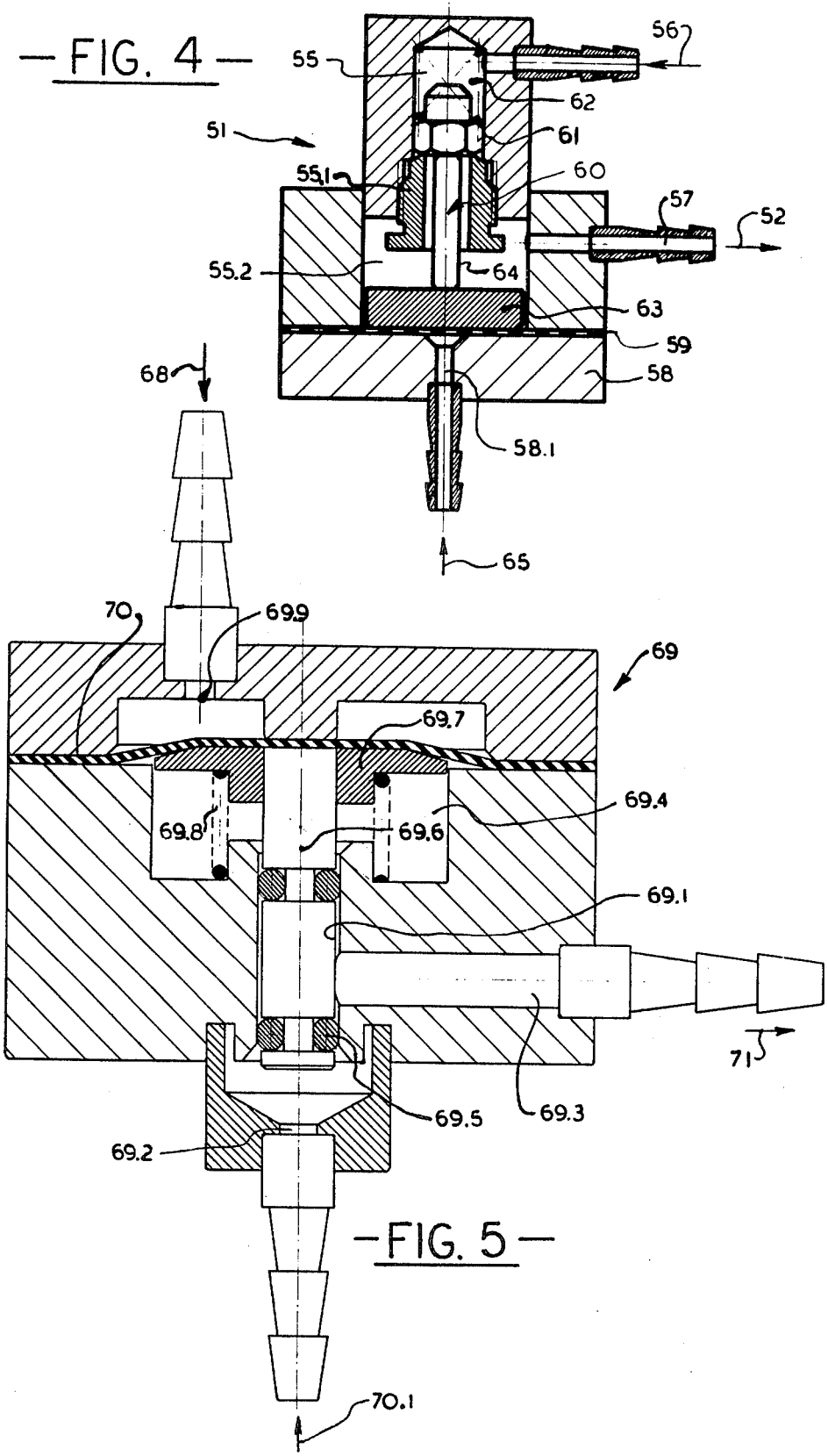

CONTROL SYSTEM FOR DENTAL DRILLS

BACKGROUND OF THE INVENTION

1. Field of the Invention

This invention relates to dental drilling equipment, and in particular to pneumatic control assemblies therefore.

2. Prior Art

In conventional pneumatically operated and controlled dental drilling apparatus, as best exemplified by apparatus described in U.S. Pat. No. 3,638,310, each hand piece has a penumatically driven turbine for operating the drill bit and air and water nozzles through which air and water can, selectively, be directed for cooling and lubricating purposes. During a drilling operation, control of pressurized air to the turbine jet and water jet is effected by operation of a foot operated valve. Prior art equipment is so arranged that air which passes through the foot valve is directed as operating air to the hand piece turbine and, selectively, by manually operated selector switches, to either the air delivery jet in the hand piece or to an air pressure operated pilot valve regulating flow of water from a pressurized water source to the water jet in the hand piece.

This type of equipment has one major problem in that, due to the length of the air conduits required to extend from the air supply and thence through the foot valve and thence back to the manifold assembly to which each hand piece is connected, pressure drop due to friction is such that the air pressure is sufficient as operating pressure for the drill turbine but is insufficient as pilot pressure for operating the water pilot valve.

SUMMARY OF THE INVENTION

The present invention provides a control assembly incorporating a diaphragm valve block as described in U.S. Pat. No. 3,638,310 for pneumatically operated dental drilling apparatus which is so arranged as to ensure availability of coolant water while drilling is in progress.

In the control assembly of the present invention, operating air, coolant air and coolant water are fed directly from a pressurized source to the hand pieces through pneumatically operated valves, all of which are operated by pilot pressure air delivered from a common pressurized air source through a common foot controlled valve so that pilot pressure sufficient to open the coolant water valve, or coolant air valve, is always available when operating air is being delivered to the hand piece turbine.

DESCRIPTION OF THE DRAWINGS

FIG. 3 is a side view of a diaphragm valve block and operating air pilot valve, FIG. 4 is a section taken on Line 4—4 of FIG. 3, FIG. 5 is a vertical central sectional view of a coolant air pilot valve.

DETAILED DESCRIPTION

Figure 1:
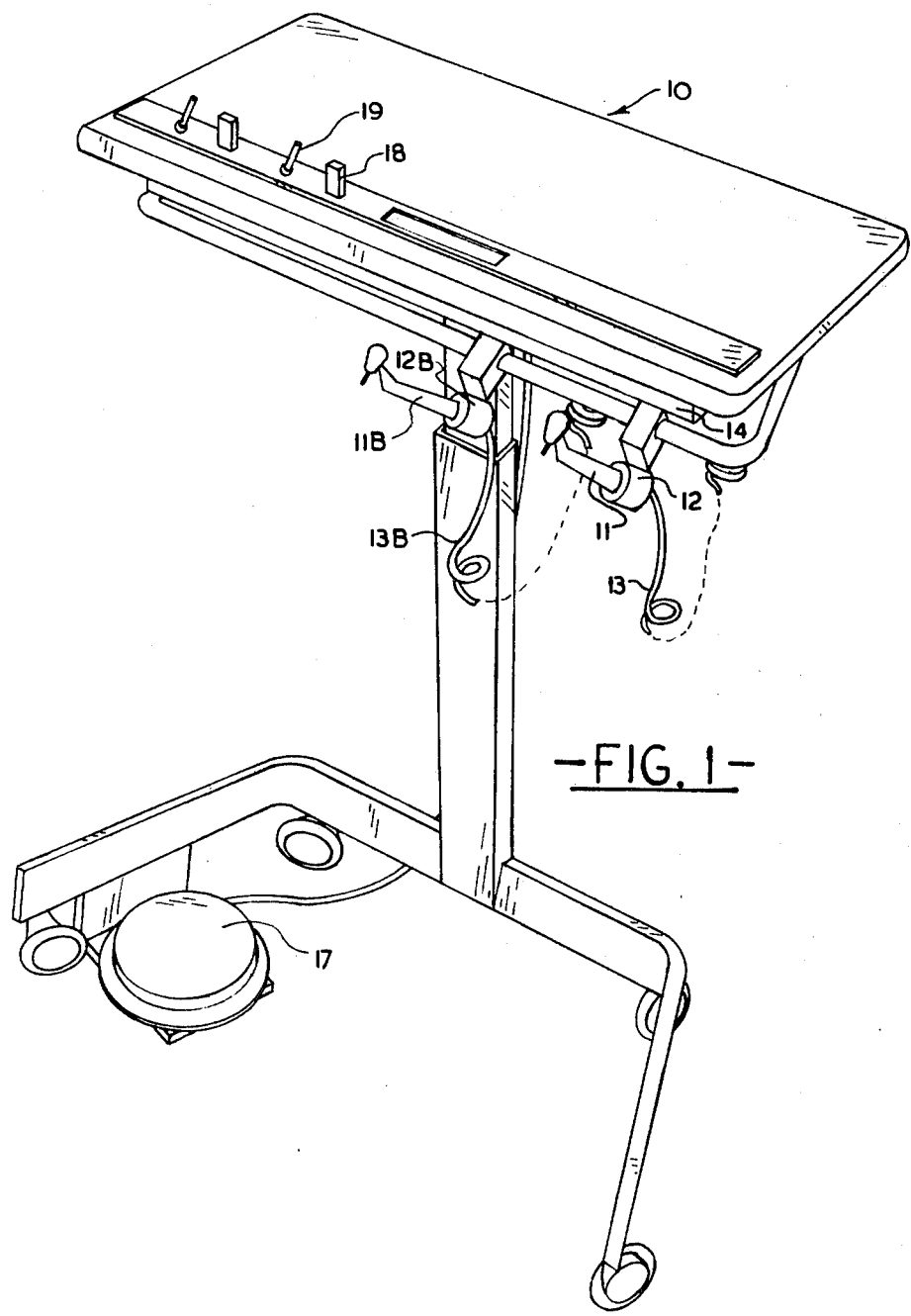
FIG. 1 is a perspective view of a dental unit showing arrangement of hand tools and foot valve.

Referring to the drawings, FIG. 1 shows the dental drilling unit 10 which is roller mounted for convenient movement around a dental chair (not shown). The unit shown has two conventional hand pieces, severally 11 and 11B, in this case being drills which are removably mounted in holders 12 and 12B. The hand pieces are connected through flexible conduit assemblies 13 and 13B and a control assembly 14 mounted on the unit, but not shown in FIG. 1, to a source of pressurized air 15 and a source of pressurized water 16. Each hand piece, when removed from its holder, is operated by operation of a conventional foot valve 17 to cause delivery of operating air to the hand piece for driving the drill bit and, selectively, by appropriate operation of valves 18 and 19 manually operated by switches 18.1 and 19.1 mounted on the unit to obtain, selectively, emission of coolant air or water during a drilling operation.

Figure 2:
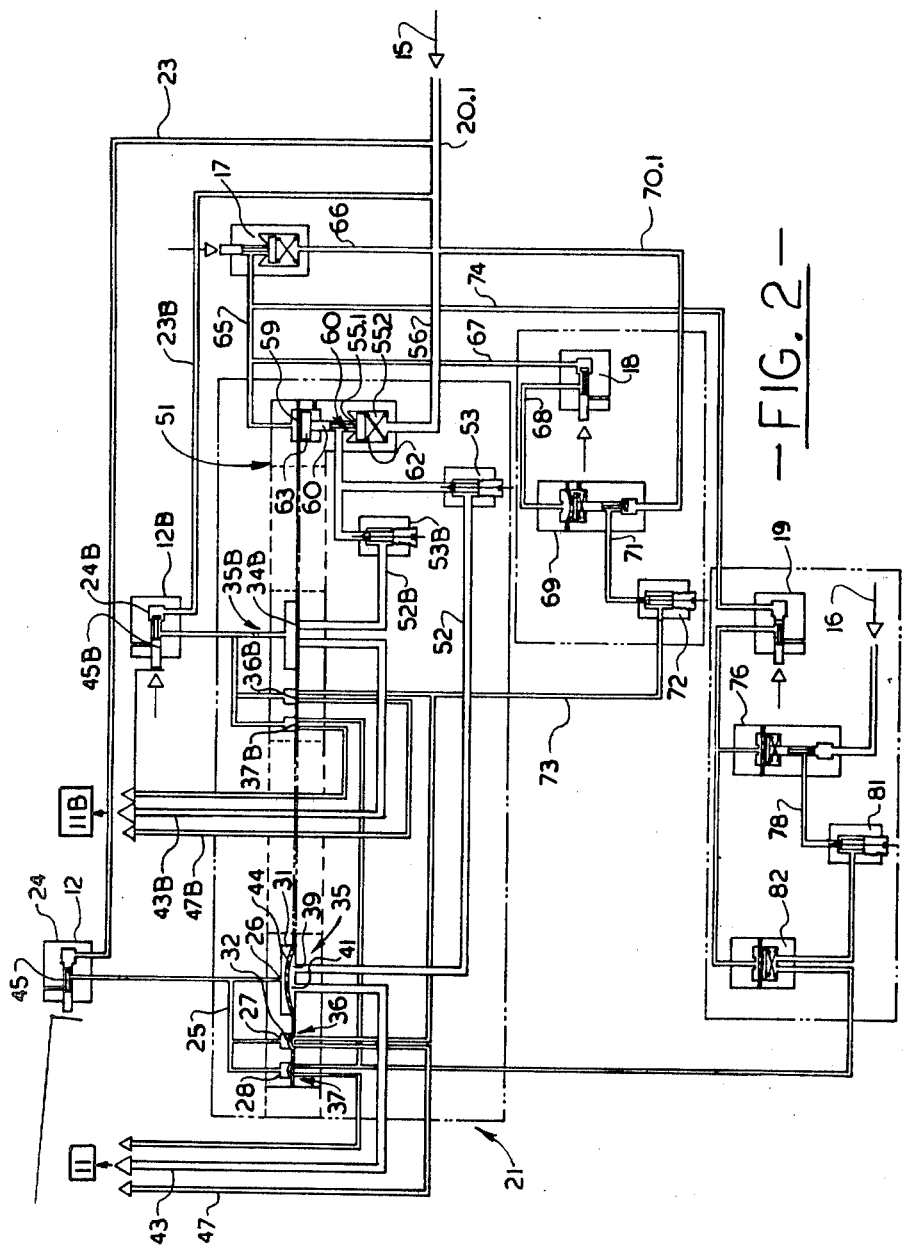
FIG. 2 is a schematic representation of the control assembly of the present invention.

FIG. 2 shows schematically a control arrangement for the hand pieces 11 and 11B. Those control elements of hand pieces 11B are accorded the same numerical references as corresponding elements of hand piece 11, followed by the letter "B".

As shown in FIG. 2, pressurized air from the pressurized source 15 delivered as signal pressure through a fitting 20 on a diaphragm valve block 21 constructed in accordance with the teachings of U.S. Pat. No. 3,638,310 (see also FIG. 3) which is mounted on the unit 10, onto a manifold 20.1 thence through a discharge fitting 22 and conduit 23 and a valve 24 operated by movement of the hand piece holder 12, as described in U.S. Pat. No. 3,638,310, to a manifold 25. The manifold 25 is ported through ports 26, 27 and 28 to chambers 31, 32 and 33, respectively, of diaphragm gate valves 35, 36 and 37 of the valve block 21. The chamber 31 has an operating air inlet port 39 and an operating air exhaust port 41, the exhaust port 41 having a fitting 42 (see FIG. 3) to which a flexible hose 43 extending to the turbine of the hand piece 11 is connected. A flexible diaphragm 44 separates the ports 26 from the inlet and exhaust ports 39 and 41 and normally closes the exhaust port 41 when signal air pressure is delivered into the chamber 31 from the manifold 25 and which when manifold 25 is exhausted to atmosphere enables pressurized operating air to pass between ports 39 and 41.

The valve 24 is a conventional three-way spool valve, the spool 45 of which is urged under signal air pressure to a normally open position in which position the manifold 25 exhausts to atmosphere and is closed to pressurized signal air delivered through the conduit 23, and is moved under weight of the hand piece 11, when the latter is placed in the holder, to a closed position in which latter position the manifold 25 receives pressurized air through the conduit 23 so as to close the port 41. The diaphragm gate valve 36 is constructed in the same manner as gate valve 35 for delivery of coolant air through a conduit 47 of the conduit assembly 13 to the hand piece 11. As shown in FIG. 2, operating and coolant air and coolant water is delivered to hand piece 11B through diaphragm gates 35B, 36B and 37B, signal air for operation of which is delivered through a valve 24B at holder 12B.

Operating air is delivered to the drill turbines of hand pieces 11 and 11B directly from the manifold 20.1 pressure 15 through a pilot valve 51 mounted on the valve block 21 and thence through conduits 52 and 52B and ports 34 and 34B, controlled by adjustable flow valves 53 and 53B. The valve 51 (see FIG. 4) has a cylindrical chamber 55 into which air from the air source 15 is directed through a conduit 56 and which opens through a valve seat 55.1 into a larger diameter cylindrical chamber 55.2 having a side wall exhaust port 57 to which the conduits 52 and 52B are connected. The chamber 55.2 has a head 58 having an air intake port 58.1 which opens into the chamber 55.1 against a flexible diaphragm 59. A valve operating element 60 has a closure element 61 urged to a normal closed position against the seat 55.1 by a spring 62 and has a piston head 63 in the chamber 55.2 connected to the closure element 61 by a stem 64 whereby upon emission of pressurized air (herein termed "pilot air") through the port 58.1 the valve can be operated to an open position to allow flow of operating air through the conduit 52. This pilot air pressure is delivered from a manifold 65 which is connected through the foot valve 17 and a conduit 66 to the source of pressurized air 15. It is seen that, although pilot air pressure and operating air pressure may be the same, the valve 51 will open when pilot air is delivered to the manifold 65 by operation of the foot valve.

Pilot air pressure is also delivered from the manifold 65 and thence through a conduit 67 to the air valve 18 which is also a spool valve similar to the spool valve 24 and which delivers pilot air through a conduit 68 to a pilot valve 69.

The pilot valve 69 (see FIG. 5) is functionally the same as valve 51 and has a small diameter cylinder 69.1 having an air inlet port 69.2 and a side wall air discharge port 69.3 and which opens into a large diameter cylinder 69.4. A piston type closure element 69.5 slidably fits in the small cylinder 69.1 and is connected by a stem 69.6 to a large diameter piston head 69.7 in the large cylinder. A compression spring 69.8 urges the valve to a normal closed position as shown. Pilot air delivered via the conduit 68 and through a port 69.9 against a flexible diaphragm 70 over the piston head opens the valve against the action of the spring 69.8. In the open position the valve enables emission of coolant air from the manifold 25 via a conduit 70.1 thence through a conduit 71 and adjustable control valve 27 to the diaphragm gates 36 and 36B.

Pilot air pressure from the manifold 65 is also directed through conduit 74 and valve 19, which is also a spool valve similar to spool valve 24, to a pilot valve 76 which is the same type of valve as valve 69, opening of which enables emission of pressurized water 16 through a conduit 78 thence through a flow control valve 81 and a water retraction valve 82 to the diaphragm gate 37. The water retraction valve is well known in the trade and need not be further described.

In operation of the control assembly and with reference to FIG. 2, the hand piece 11 has been removed from its holder for use which thus enables the spool 45 of valve 24 to operate to a position in which it closes manifold 25 to signal air pressure and then opens the manifold 25 to atmosphere. The coolant air valve 18 has also been operated to enable pilot pressure to be applied to valve 69 to open the conduit 73 to the diaphragm gate 36. The water valve 19, however, is positioned to prevent application of pilot pressure to valve 76. The control assembly will therefore, enable operating air and coolant air to be delivered to the hand piece 11 when ever the foot valve is operated to an open position. It will be seen, however, that with respect to hand piece 11B which remains in its holder, the valve 23B admits signal air pressure to the diaphragm gates 35B, 36B and 37B so that neither air nor water can be delivered to the hand piece 11B.

The pilot valves 51, 69 and 76 are adjusted so as to have the same opening pilot pressure which conventionally is less than source air pressure. Pressure variation in the manifold 65 will affect all pilot valves equally and thus ensure that if there is sufficient pilot pressure to open the valve 51 to enable operating air to pass through the drill turbine, then there will be sufficient pilot pressure to open the valves 69 and 76 to enable the flow of water of coolant air to the hand piece 11.

I claim:

1. A control assembly for controlling flow of operating air from a source of pressurized air and coolant fluid from a source of pressurized coolant to a pneumatically driven dental hand tool of dental drilling apparatus comprising:
   (a) first conduit means for delivery operating air from the pressurized air source to the hand piece,
   (b) second conduit means for delivering pressurized coolant fluid from the pressurized fluid source to the hand piece,
   (c) a pilot valve in each of the conduit means for controlling passage of operating air and coolant fluid there-through,
   (d) each pilot valve having:
      (i) a closure element spring-urged to a normal closed position,
      (ii) a closed chamber,
      (iii) a valve operator in the closed chamber for moving the closure element to an open position upon application of air at selected pilot pressure to the chamber,
   (e) a pilot air conduit means between the source of pressurized air and the chamber of each pilot valve,
   (f) a foot-operated valve in said pilot air conduit means for controlling delivery of pilot air to the pilot valves,
   (g) said pilot valves being arranged to open at the same selected pilot pressure so as to enable concurrent delivery of coolant fluid and operating air to the hand piece.

2. A control assembly as claimed in claim 1 including:
   (a) a diaphragm gate valve assembly in said first and second conduit means downstream of each pilot valve for controlling passage of operating air and coolant fluid to the hand piece, said diaphragm gate valve assembly being operable to a closed position under application of air at a selected signal pressure and operable to an open position under air at atmospheric pressure,
   (b) a feed line extending between the source of pressurized air and the diaphragm gate valve assembly for delivering air at signal pressure to the diaphragm gate valve assembly,
   (c) valve means in the feed line for controlling passage or signal air there-through, being operable to a first position in which the feed line is open to apply air signal pressure to the diaphragm gate valve assembly and a second position in which the feed line is closed,
   (d) a hand piece holder adapted to receive the hand piece for storage,
   (e) a valve operator associated with the holder for operating the valve means to a said first position when the hand piece is removed from the holder and for operating the valve means to said second position when the hand piece is applied to the holder.

3. A control assembly as claimed in claim 1 including a hand operated valve upstream of the pilot valve in the second conduit means selectively operable between open and closed positions for controlling the passage of coolant fluid through said second conduit means.

* * * * *